United States Patent [19]

Samson et al.

[11] Patent Number: 4,538,622
[45] Date of Patent: Sep. 3, 1985

[54] GUIDE WIRE FOR CATHETERS

[75] Inventors: Wilfred J. Samson, Saratoga; Ronald G. Williams, Mountain View, both of Calif.

[73] Assignee: Advanced Cardiovascular Systems, Inc., Mountain View, Calif.

[21] Appl. No.: 550,917

[22] Filed: Nov. 10, 1983

[51] Int. Cl.³ .................... A61B 10/00; A61M 25/00
[52] U.S. Cl. .................................. 128/772; 128/657; 604/170
[58] Field of Search ............... 128/772, 656–658; 604/95, 164, 170, 280–283

[56] References Cited

U.S. PATENT DOCUMENTS

| | | | |
|---|---|---|---|
| 3,789,841 | 2/1974 | Antoshkiw | 128/772 |
| 3,941,119 | 3/1976 | Corrales | 128/657 |
| 4,003,369 | 1/1977 | Heilman et al. | 128/772 |
| 4,020,829 | 5/1977 | Wilson et al. | 128/657 |

FOREIGN PATENT DOCUMENTS 0014424  8/1980  European Pat. Off. ............ 128/772

*Primary Examiner*—Stephen C. Pellegrino
*Attorney, Agent, or Firm*—Flehr, Hohbach, Test, Albritton and Herbert

[57] ABSTRACT

Guide wire comprising an elongate flexible cylindrical element formed of metallic material having high torsional capability and having a proximal portion ranging from 0.008 to 0.020 inches and a distal portion having a diameter of less than 0.007 inches. It also comprises a coil formed of metallic material and secured to the distal portion and an additional coil formed of a material which is different from the material of which the first named coil is formed and which is substantially radiopaque secured to the distal extremity of the first named coil. In addition, it comprises a tip having a rounded conformation secured to the distal extremity of the last named coil.

10 Claims, 3 Drawing Figures

U.S. Patent   Sep. 3, 1985   4,538,622
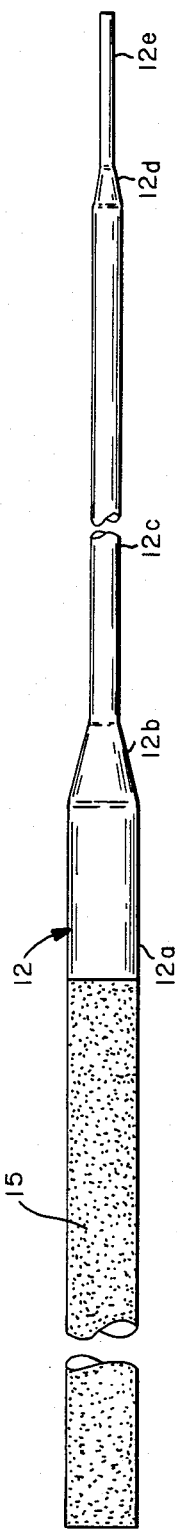
FIG.—1
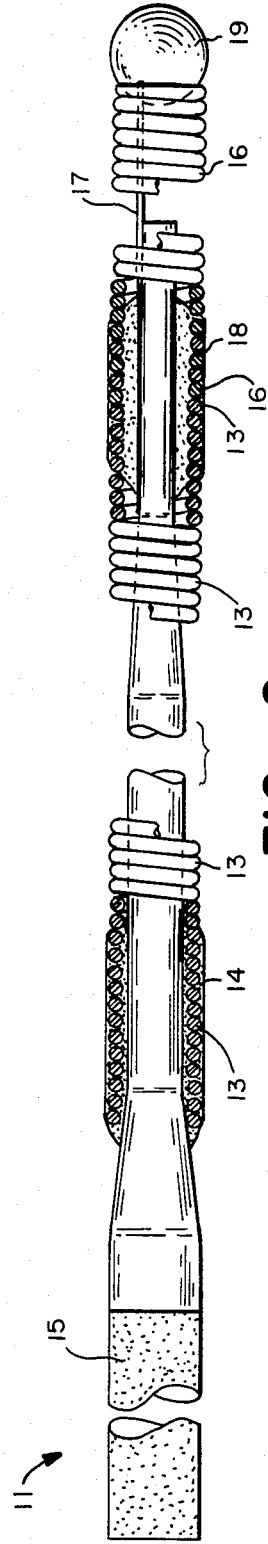
FIG.—2
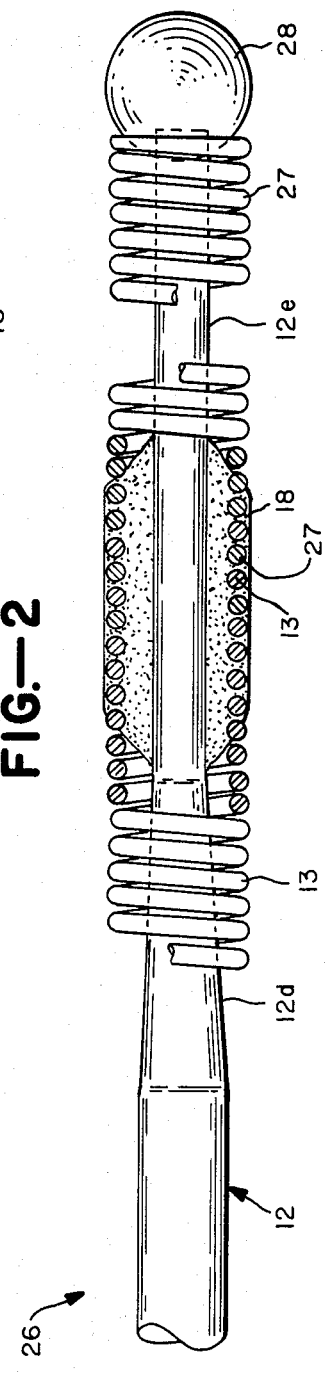
FIG.—3

GUIDE WIRE FOR CATHETERS

This invention relates to guide wires for use in introducing catheters into vascular systems and more particularly to cardiovascular systems in humans.

Guide wires heretofore have been provided to facilitate insertion of catheters into cardiovascular systems. One such guide wire is disclosed in application Ser. No. 513,222, filed on July 13, 1983. It has been found that with such guide wires it has been difficult to introduce such guide wires into very small vessels and particularly into partially occluded segments of such vessels. There is therefore a need for an improved guide wire which can be successfully introduced into small vessels in the cardiovascular system.

It is a general object of the present invention to provide a guide wire for catheters which can be introduced into small vessels in vascular systems and particularly cardiovascular systems in humans.

Another object of the invention is to provide a guide wire of the above character which has high torque capabilities.

Another object of the invention is to provide a guide wire of the above character which has a very floppy distal end.

Another object of the invention is to provide a guide wire of the above character which can be provided with various degrees of floppiness on its distal end.

Additional objects and features of the invention will appear from the following description of preferred embodiments as set forth in detail in conjunction with the accompanying drawings.

FIG. 1 is a side elevational view of a core wire used in connection with construction of a guide wire incorporating the present invention.

FIG. 2 is a side elevational view partially in cross section of a guide wire incorporating the present invention and which is provided with a floppy distal end.

FIG. 3 is a side elevational view partially in cross section of another embodiment of a guide wire incorporating the present invention with a less floppy distal end.

The guide wire for use with catheters consists of a flexible cylindrical elongate element formed of stainless steel and having a proximal portion having a diameter ranging from 0.008 to 0.020 inches and a distal portion having a diameter of less than 0.007 inches. A coil formed of stainless steel to prevent permanent deformation of the elongate element is secured to the distal portion of the elongate element and an additional coil formed of material which is substantially radiopaque is secured to the coil of stainless steel.

The guide wire 11 incorporating the invention shown in FIGS. 1 and 2 consists of a flexible elongate cylindrical element 12 formed of a suitable metallic material having high torsional strength such as stainless steel. It should be appreciated that if desired other materials can be utilized other than stainless steel, for example certain carbon steel could be used as well as titanium and beryllium copper. The elongate cylindrical element can be in the form of a wire-like hollow cylindrical element or in the form of a wire-like cylindrical solid core.

The wire which is utilized for forming the elongate cylindrical element 12 can be formed in a suitable manner as, for example from No. 304 stainless steel including 20% chromium and 10% nickel and having a minimum of 240 ksi tensile strength. It can be workhardened by drawing 0.150 stainless steel wire material down to 0.016 material. The wire can then be straightened and cut to the desired lengths. Thereafter, it can be annealed after which it can be centerless ground to provide the flexible elongate element shown in FIG. 1.

As shown in particular in FIG. 1, the flexible elongate cylindrical element 12 is provided with a cylindrical portion 12a having a suitable diameter such as from 0.008 to 0.020 inches and preferably a diameter of approximately 0.016 inches. It is provided that with a tapered portion 12b which adjoins one extremity of the cylindrical portion 12a which adjoins another cylindrical portion 12c having a suitable dimension such as 0.005 to 0.010 inches and preferably a thickness of approximately 0.008 inches. Another tapered portion 12d is provided which adjoins the cylindrical portion 12c. Another cylindrical portion 12e adjoins the tapered portion 12d. The cylindrical portion 12e has a suitable dimension less than 0.007 inches such as 0.003 inches±0.0005 inches.

The overall flexible elongate element can have a suitable length of a range from 150 to 250 centimeters but preferably has a length of approximately 175 centimeters. Cylindrical portion 12e can have a length ranging from 2 to 6 centimeters and preferably has a length of approximately 4 centimeters. Portion 12c can have a length ranging from 25 to 30 centimeters and preferably has a length of approximately 26.5 centimeters. The tapered portion 12d can have a length of approximately one-half of a centimeter whereas the tapered portion 12b can have a length of approximately 1 centimeter.

The proximal end of the elongate flexible element 12 is coated with a suitable material so as to facilitate movement of the guide wire hereinafter described through the coronary vessels. For example a substantial portion of the cylindrical portion 12a can be coated with a Teflon coating 15 to suitable thickness, for example a thickness of 0.001 inches.

An elongate coil 13 of a suitable material such stainless steel is secured to the distal extremity of the cylindrical element 12 by suitable means such as the use of solder 14 as shown particularly in FIG. 2. As shown, the coil 13 extends over the cylindrical portion 12c and the solder joint 14 between the flexible element 12 and the elongate coil 13 is formed in the vicinity of the tapered portion 12b.

The coil 13 is formed from stainless steel wire having a diameter of approximately 0.003 and is wound so that the coil has an outer diameter of approximately 0.017 inches. The coil 13 is wound in such a manner so that the coils are tightly packed or in other words "bottomed out". The solder 14 is applied to the coil in such amounts so that it fills interstices between the coil but does not significantly increase the outer diameter of the coil. The coil 13 extends towards the distal end of the elongate element 12 into a region which is adjacent the cylindrical portion 12e.

Another elongate coil 16 formed of a material which is substantially opaque to X-rays is provided. It should be formed of a material which has a density of at least 13 gm/cm$^3$. Suitable materials meeting this requirement include gold, tantalum, tungsten, platinum, iridium, rhenium and alloys of these materials. The wire which is utilized for the elongate coil 16 is formed of a platinum alloy and has suitable dimensions but preferably has dimensions which are substantially identical to the dimensions of the stainless steel coil 13. For that reason the wire would have a diameter of 0.003 inches and would be wound so that the coil would have an outside diameter of approximately 0.017 inches. One end of the elongate platinum coil 16 is threaded or screwed into the distal extremity of the elongate stainless steel coil 13 as shown particularly in FIG. 2 in such a manner so that alternate turns of the coil 16 are disposed between alternate turns of the coil 13. This screwed connection is represented by the cross-sectional lines in FIG. 2, where the cross-sectional lines for the stainless steel extend in one direction and the cross-sectional lines for the platinum extend in a direction which is displaced by 90°. In order to provide additional flexibility in the platinum coil 16, the turns of the coil rather than being tightly packed or "bottomed out" are spaced apart a suitable distance as for example 0.005 to 0.0015 inches. Alternatively, the two coils 13 and 16 can be butted together.

A safety ribbon 17 formed of a suitable material such as tungsten of suitable dimensions such as a width of 0.003 inches and a thickness of 0.001 inches extends from the extremity of the elongate cylindrical element 12 to the outermost or distal extremity of the coil 16. The proximal extremity of the safety ribbon 17 and the two ends of the coils 13 and 16 which have been screwed or butted together are joined into a unitary assembly with the elongate element 12 by suitable means such as brazing 18. As with respect to the solder joint 14, the brazing joint 18 is formed in such a manner so that the material fills the interstices between the coils 16. The brazing 18 secures the proximal extremity of the safety wire 17 to the cylindrical portion 12e of the elongate element 12.

As shown in FIG. 2, the coil 16 extends a suitable distance beyond the distal extremity of the element 12, as for example a length of 1 to 2 centimeters from the end and preferably 1.5 centimeters from the end. The distal extremity of the coil 16 is provided with suitable means for rounding off the extremity as well as securing the distal extremity of the safety wire 17 and consists of a ball or plug 19 formed of a suitable material such as gold which is bonded onto the distal end of platinum coil 16 and the distal extremity of the ribbon 17.

The solder and brazing materials utilized in connection with the manufacture of the guide wire shown in FIGS. 1 and 2 are of conventional types. For example, the solder can be a conventional copper, silver alloy or a ton silver alloy whereas the brazing material can be an alloy of silver, copper, tin and nickel.

The gide wire hereinbefore described can be characterized as being a floppy wire since it is provided with a very flexible distal extremity which can be utilized for exploring vessels in the caridovascular system to facilitate the introduction of balloon-type catheters in a manner well known to those skilled in the art. The conformation of the guide wire can readily follow the vessels in the cardiovascular system. The travel can also be observed by the use of a conventional fluoroscope.

Another guide wire incorporating the invention which has slightly less flexibility or floppiness in the guide wire shown in FIGS. 1 and 2 is shown in FIG. 3. The guide wire 26 shown in FIG. 3 consists of an elongate cylindrical element 12 of the type hereinbefore described in conjunction with FIGS. 1 and 2. Similarly, a coil 13 formed of stainless steel in the manner hereinbefore described in the embodiment shown in FIGS. 1 and 2 is utilized and is bonded to the flexible elongate element 12 by the solder 14 hereinbefore described. A coil 27 formed of platinum in the same manner as the coil 16 was formed is provided, however, the coil 17 has a lesser length than the coil 16 so that it only extends to the distal end of the elongate flexible element 12. The coil 27 is again threaded into the distal extremity of the coil 13 and is bonded to the elongate element 12 by brazing 18. Since coil 27 does not extend beyond the end of the flexible elongate element 12, it is not necessary to provide the safety wire 17 which is provided in the embodiment shown in FIGS. 1 and 2. A plug or ball 28 formed of a suitable material such as gold is formed on the distal extremity of the coil 17 and is also bonded to the distal extremity of the flexible elongate element 12. As in the previous embodiment, to provide additional flexibility the turns of the coil 27 on the outer extremity can be spaced apart as for example a distance of 0.0005 to 0.0015 inches.

From the foregoing it can be seen that there has been provided guide wires with varying degrees of flexibility so that guide wires of different capabilities can be provided to negotiate the various types of vessels which are encountered in cardiovascular systems and particularly vessels which are partially occluded. Guide wires of this type facilitate negotiating such occlusions to facilitate introduction of balloon catheters in a manner well known to those skilled in the art. The coils provided inhibit permanent deformation of the guide wire.

What is claimed:

1. In a guide wire, an elongate solid flexible cylindrical element formed of metallic material having high torsional capability and having a proximal portion ranging from 0.008 to 0.020 inches a distal portion having a diameter of less than 0.007 inches and an intermediate tapered portion, a coil formed of metallic material and secured to said distal portion and an additional coil formed of a material which is different from the material of which the first named coil is formed means, securing the proximal extremity of the additional coil to the distal extremity of the first named coil and means having a rounded conformation secured to the distal extremity of the last named coil, the additional coil being formed so that it is more flexible than the first named coil and being substantially radiopaque.

2. A guide wire as in claim 1 wherein the distal extremity of the additional coil extends beyond the distal extremity of the flexible elongate cylindrical element together with a safety wire secured to the distal extremity of the additional coil and also secured to the flexible elongate element, the safety wire having a width which is greater than the thickness.

3. A guide wire as in claim 2 wherein said means forming a rounded conformation on the outer extremity of the additional coil is bonded to the distal extremity of the flexible elongate cylindrical element.

4. In a guide wire, an elongate flexible cylindrical element formed of metallic material having high torsional capability and having a proximal portion ranging from 0.008 to 0.020 inches and a distal portion having a diameter of less than 0.007 inches, a coil formed of metallic material and secured to said distal portion and an additional coil formed of a material which is different from the material of which the first named coil is formed and which is substantially radiopaque secured to the distal extremity of the first named coil and means having a rounded conformation secured to the distal extremity of the last named coil, wherein said first and second named coils being screwed together so that at least portions of the coils have individual alternate turns which are disposed between each other.

5. A guide wire as in claim 4 wherein the portion which are screwed together are brazed together and are brazed to the flexible elongate element.

6. In a guide wire, an elongate flexible cylindrical element formed of metallic material having high torsional capability and having a proximal portion ranging from 0.008 to 0.020 inches and a distal portion having a diameter of less than 0.007 inches, a coil formed of metallic material and secured to said distal portion and an additional coil formed of a material which is different from the material of which the first named coil is formed and which is substantially radiopaque secured to the distal extremity of the first named coil, means having a rounded conformation secured to the distal extremity of the last named coil, the second named coil extending beyond the distal extremity of the flexible elongate element and a safety wire, one end of the safety wire being brazed to the flexible longate element and the other end of the safety wire being bonded to the means forming a rounded conformation on the outer extremity of the second named coil.

7. A guide wire as in claim 1 wherein said first named coil is formed of stainless steel and wherein said second named coil is formed of a platinum alloy.

8. In a guide wire, an elongate flexible metallic element, a coil carried by said elongate flexible metallic element, said coil being formed of first and second sections, said first and second sections having end portions adjoining each other and means forming a bond between the ends of said first and second sections and a portion of said flexible elongate metallic element and a rounded protrusion carried by the distal extremity of the coil.

9. A guide wire as in claim 8 wherein said first and second coil sections have their ends screwed together.

10. A guide wire as in claim 9 together with a safety wire extending from the flexible elongate element and the rounded protrusion and being bonded thereto.

* * * * *

UNITED STATES PATENT AND TRADEMARK OFFICE
CERTIFICATE OF CORRECTION

PATENT NO. : 4,538,622
DATED : September 3, 1985
INVENTOR(S) : Wilfred J. Samson and Ronald G. Williams It is certified that error appears in the above—identified patent and that said Letters Patent is hereby corrected as shown below:

Column 4,
    Claim 1, line 31, insert --,-- after the word "inches"
    Claim 1, line 36, insert --,-- after the word "formed"; delete "," after the word "means"

Claim 4, line 65, delete the word "wherein" after the word "coil".

Signed and Sealed this
Ninth Day of December, 1986

*Attest:*

DONALD J. QUIGG

*Attesting Officer*    *Commissioner of Patents and Trademarks*